US011776128B2

(12) United States Patent
Yoo et al.

(10) Patent No.: US 11,776,128 B2
(45) Date of Patent: Oct. 3, 2023

(54) AUTOMATIC DETECTION OF LESIONS IN MEDICAL IMAGES USING 2D AND 3D DEEP LEARNING NETWORKS (71) Applicant: Siemens Healthcare GmbH, Erlangen (DE)

(72) Inventors: Youngjin Yoo, Princeton, NJ (US); Pascal Ceccaldi, New York, NY (US); Eli Gibson, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 174 days.

(21) Appl. No.: 17/118,668

(22) Filed: Dec. 11, 2020

(65) Prior Publication Data

US 2022/0189028 A1 Jun. 16, 2022

(51) Int. Cl.
*G06T 7/11* (2017.01)
*G06T 7/00* (2017.01)
(Continued)

(52) U.S. Cl.
CPC .............. *G06T 7/11* (2017.01); *G06N 3/045* (2023.01); *G06N 3/08* (2013.01); *G06T 7/0012* (2013.01);
(Continued)

(58) Field of Classification Search
CPC .............. G06T 7/0012; G06T 7/11; G06T 2207/20081; G06T 2207/30096;
(Continued)

(56) References Cited

U.S. PATENT DOCUMENTS 10,452,960 B1\* 10/2019 Li ............................ G06N 3/08
2014/0266678 A1\* 9/2014 Shapiro .............. G05B 23/0272
340/514
(Continued)

FOREIGN PATENT DOCUMENTS

CN 106600571 A 4/2017
CN 107016681 A 8/2017

OTHER PUBLICATIONS

Ronneberger et al., "U-net: Convolutional Networks for Biomedical Image Segmentation," 2015, Medical Image Computing and Computer-Assisted Intervention—MICCAI 2015, Lecture Notes in Computer Science, vol. 9351, 8 pgs.
(Continued)

*Primary Examiner* — Ajibola A Akinyemi (57) ABSTRACT

Systems and methods for automatic segmentation of lesions from a 3D input medical image are provided. A 3D input medical image depicting one or more lesions is received. The one or more lesions are segmented from one or more 2D slices extracted from the 3D input medical image using a trained 2D segmentation network. 2D features are extracted from results of the segmentation of the one or more lesions from the one or more 2D slices. The one or more lesions are segmented from a 3D patch extracted from the 3D input medical image using a trained 3D segmentation network. 3D features are extracted from results of the segmentation of the one or more lesions from the 3D patch. The extracted 2D features and the extracted 3D features are fused to generate final segmentation results. The final segmentation results are output.

18 Claims, 9 Drawing Sheets

(51) Int. Cl.
| | |
|---|---|
| *G16H 30/40* | (2018.01) |
| *G16H 50/50* | (2018.01) |
| *G16H 50/20* | (2018.01) |
| *G06N 3/08* | (2023.01) |
| *G06N 3/045* | (2023.01) |

(52) U.S. Cl.
CPC ............ *G16H 30/40* (2018.01); *G16H 50/20* (2018.01); *G16H 50/50* (2018.01); *G06T 2207/10088* (2013.01); *G06T 2207/20076* (2013.01); *G06T 2207/20081* (2013.01); *G06T 2207/20084* (2013.01); *G06T 2207/30016* (2013.01); *G06T 2207/30096* (2013.01)

(58) Field of Classification Search
CPC . G06T 2207/10081; G06T 2207/20084; G06T 2207/10088; G06T 2207/10072; G06T 2207/10132; G06T 2207/30004; G06T 2207/30101; G06T 2207/20076; G06T 7/12; G06T 7/0016; G06T 2207/20104; G06T 2207/10116; G06T 7/0014
USPC ....................................................... 382/131
See application file for complete search history.

(56) References Cited

U.S. PATENT DOCUMENTS

| | | | |
|---|---|---|---|
| 2017/0147908 | A1 | 5/2017 | Chen et al. |
| 2019/0130562 | A1* | 5/2019 | Liu ................ G06V 20/64 |
| 2019/0287242 | A1* | 9/2019 | Zhang ............. G06T 7/11 |
| 2021/0365717 | A1* | 11/2021 | Cao ................ G06N 3/08 |

OTHER PUBLICATIONS

Singh et al., "3D Deep Learning on Medical Images: A Review," 2020, arXiv preprint arXiv:2004.00218, 26 pgs.
Xu et al., "Orchestral Fully Convolutional Networks for Small Lesion Segmentation in Brain MRI," 2018, IEEE 15th International Symposium on Biomedical Imaging, pp. 889-892.
Kamnitsas et al., "Efficient Multi-Scale 3D CNN with Fully Connected CRF for Accurate Brain Lesion Segmentation," 2017, Medical Image Analysis, vol. 36, pp. 61-78.
Dikici et al., "Automated Brain Metastases Detection Framework for T1-Weighted Contrast-Enhanced 3D MRI," 2020, IEEE Journal of Biomedical and Health Informatics, vol. 24, Issue: 10, pp. 2883-2893.
Grøvik et al., "Deep Learning Enables Automatic Detection and Segmentation of Brain Metastases on Multisequence MRI," 2020, Journal of Magnetic Resonance Imaging 51(1), pp. 175-182.
Bousabarah et al., "Deep convolutional neural networks for automated segmentation of brain metastases trained on clinical data," 2020, Radiation Oncology 15, pp. 1-9.
Zhang et al., "Deep-Learning Detection of Cancer Metastases to the Brain on MRI," 2020, Journal of Magnetic Resonance Imaging, pp. 1-10.
Sunwoo et al., "Computer-aided detection of brain metastasis on 3D MR imaging; Observer performance study," 2017, PLoS One 12(6), pp. 1-18.
Charron et al., "Automatic detection and segmentation of brain metastases on multimodal MR images with a deep convolutional neural network," 2018, Computers in Biology and Medicine, vol. 95, pp. 43-54.

* cited by examiner

Receive a 3D input medical image depicting one or more lesions
202

Segment the one or more lesions from one or more 2D slices extracted from the 3D input medical image using a trained 2D segmentation network
204

Extract 2D features from results of the segmentation of the one or more lesions from the one or more 2D slices
206

Segment the one or more lesions from a 3D patch extracted from the 3D input medical image using a trained 3D segmentation network
208

Extract 3D features from results of the segmentation of the one or more lesions from the 3D patch
210

Fuse the extracted 2D features and the extracted 3D features to generate final segmentation results
212

Output the final segmentation results
214

|  | 2.5D U-Net | 3D patch-based U-Net | Weakly-supervised fusion |
| --- | --- | --- | --- |
| Precision | 0.31 | 0.21 | 0.75 |
| Recall | 0.83 | 0.91 | 0.74 |
| F1-score | 0.45 | 0.34 | 0.74 |

AUTOMATIC DETECTION OF LESIONS IN MEDICAL IMAGES USING 2D AND 3D DEEP LEARNING NETWORKS

TECHNICAL FIELD

The present invention relates generally to the automatic detection of lesions in medical images, and in particular to the automatic detection of lesions in medical images using both 2D and 3D deep learning networks.

BACKGROUND

Brain metastases are lesions that are common in intracranial cancers in adults. Brain MRI (magnetic resonance imaging) is the standard imaging modality for diagnosis, surgery planning, radiation treatment planning, and monitoring of therapy response for brain metastases. The detection and delineation of brain metastases in brain MRI images has emerged as a limiting factor in effectively managing brain metastases. In particular, manual detection and delineation of brain metastases in brain MRI images by neurologists or radiologists is a time consuming and expensive task, and can suffer from intra- and inter-expert variability. Recently, deep learning methods for automatic detection and segmentation of brain metastases have been proposed. However, the detection sensitivity of such deep learning methods is too limited for use in clinical applications.

BRIEF SUMMARY OF THE INVENTION

In accordance with one or more embodiments, systems and methods for automatic segmentation of lesions from a 3D input medical image are provided using both a 2D segmentation network and a 3D segmentation network. Such automatic segmentation of lesions using both a 2D segmentation network and a 3D segmentation network enables the exploitation of the high-resolution 2D context from 2D slice images and through-plane features from 3D patches. Accordingly, the automatic segmentation of lesions in accordance with embodiments described herein provide for segmentation results with high sensitivity and high specificity as compared to conventional approaches.

In accordance with one embodiment, systems and methods for automatic segmentation of lesions from a 3D input medical image are provided. A 3D input medical image depicting one or more lesions is received. The one or more lesions are segmented from one or more 2D slices extracted from the 3D input medical image using a trained 2D segmentation network. 2D features are extracted from results of the segmentation of the one or more lesions from the one or more 2D slices. The one or more lesions are segmented from a 3D patch extracted from the 3D input medical image using a trained 3D segmentation network. 3D features are extracted from results of the segmentation of the one or more lesions from the 3D patch. The extracted 2D features and the extracted 3D features are fused to generate final segmentation results. The final segmentation results are output.

In one embodiment, extracting the 2D features comprises extracting probability values from a prediction map output from the trained 2D segmentation network and extracting the 3D features comprises extracting probability values from a prediction map output from the trained 3D segmentation network.

In one embodiment, the extracted 2D features and the extracted 3D features are fused using a trained machine learning based fusion model. The trained machine learning based fusion model may be trained by ensemble learning. The extracted 2D features and the extracted 3D features may be fused by concatenating the extracted 2D features and the extracted 3D features or by combining the extracted 2D features and the extracted 3D features based on a weighted vote. The extracted 2D features and the extracted 3D features are fused to generate a final prediction map representing a voxelwise score that a voxel depicts a lesion.

In one embodiment, the 3D input medical image comprises an MRI (magnetic resonance imaging) image of a brain of a patient and the one or more lesions comprises one or more brain metastases. The one or more 2D slices may comprise a plurality of orientation images.

These and other advantages of the invention will be apparent to those of ordinary skill in the art by reference to the following detailed description and the accompanying drawings.

DETAILED DESCRIPTION

The present invention generally relates to the automatic detection of lesions in medical images using both a trained 2D (two dimensional) segmentation network and a trained 3D (three dimensional) segmentation network. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for the automatic segmentation of lesions from a medical image by applying both a trained 2D segmentation network and a trained 3D segmentation network and fusing features extracted from results of the segmentation by the trained 2D segmentation network and the trained 3D segmentation network. Advantageously, embodiments described herein provide for the automatic segmentation of lesions with a high specificity due to the full field-of-view 2D slice that is input into the trained 2D segmentation network and with a high sensitivity due to the high dimensionality of the 3D patch that is input into the trained 3D segmentation network.

Figure 1:
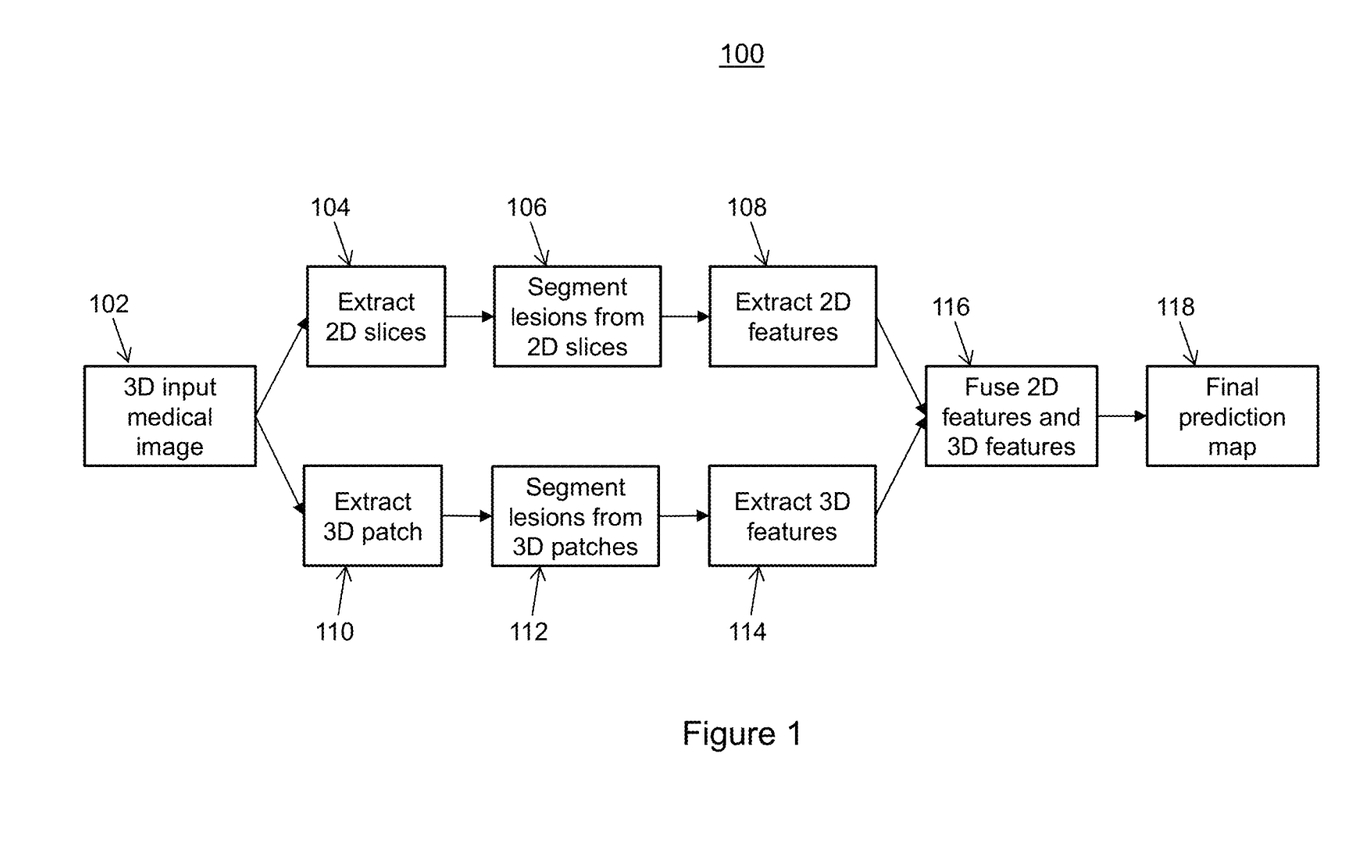
FIG. 1 shows a workflow for automatic segmentation of lesions from a 3D medical image, in accordance with one or more embodiments.
Figure 2:
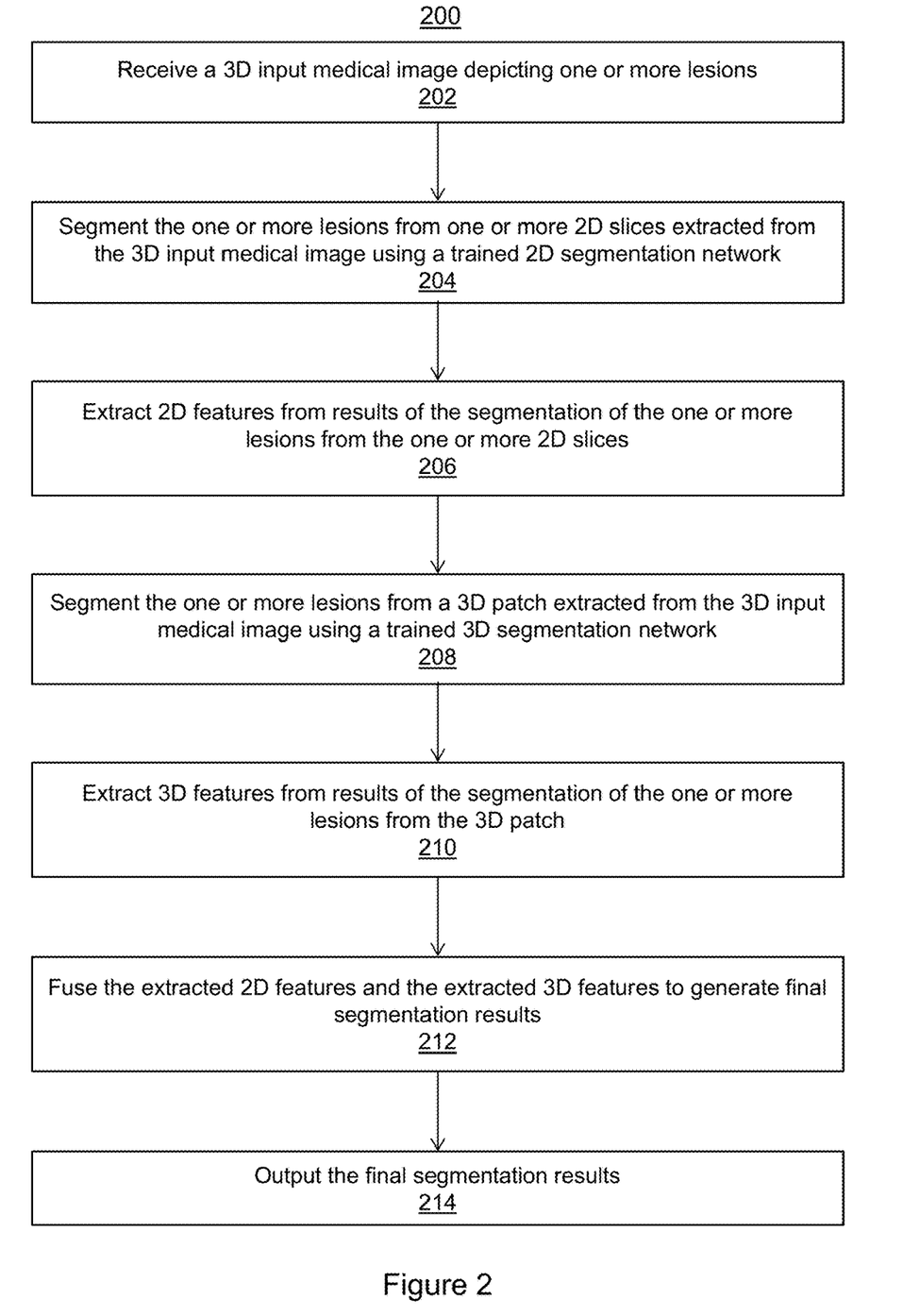
FIG. 2 shows a method for automatic segmentation of lesions from a 3D medical image, in accordance with one or more embodiments.

FIG. 1 shows a workflow 100 for automatic segmentation of lesions from a 3D medical image, in accordance with one or more embodiments. FIG. 2 shows a method 200 for automatic segmentation of lesions from a 3D medical image, in accordance with one or more embodiments. FIG. 1 and FIG. 2 will be described together. The steps of method 200 of FIG. 2 may be performed by one or more suitable computing devices, such as, e.g., computer 902 of FIG. 9.

At step 202, a 3D input medical image depicting one or more lesions is received. In one example, the 3D input medical image may be 3D input medical image 102 in FIG. 1. The 3D input medical image may be of the brain of a patient and may depict one or more brain metastases. However, the 3D input medical image may be of any anatomical object of interest of the patient and may depict one or more lesions or abnormalities of any type.

In one embodiment, the 3D input medical image is a 3D MRI (magnetic resonance imaging) image. However, the 3D input medical image may be of any suitable modality, such as, e.g., MPRAGE (magnetization prepared rapid gradient echo imaging), CT (computed tomography), US (ultrasound), x-ray, or any other modality or combination of modalities. The 3D input medical image may be received directly from an image acquisition device, such as, e.g., a MRI scanner, as the 3D input medical image is acquired, or can be received by loading a previously acquired 3D input medical image from a storage or memory of a computer system or receiving a 3D input medical image that has been transmitted from a remote computer system.

At step 204, the one or more lesions are segmented from one or more 2D slices extracted from the 3D input medical image using a trained 2D segmentation network. In one example, the one or more 2D slices are extracted at block 104 of FIG. 1 from 3D input medical image 102 and the lesions are segmented from 2D slices at block 106 of FIG. 1. The one or more 2D slices are 2D cross sectional images of the 3d input medical image. The one or more 2D slices may comprise a single 2D slice depicting the one or more lesions. Alternatively, the one or more 2D slices may also comprise a plurality of 2D slices depicting the one or more lesions. In one embodiment, a 2.5D image (two dimensions plus time) may be formed based on the plurality of 2D slices, in which case the trained 2D segmentation network is a 2.5D segmentation network. The 2.5D image may be formed based on a plurality of 2D slices acquired from an out-of-plane direction (e.g., the z axis in 3D). In one embodiment, the one or more 2D slices are full field-of-view orientation images, such as, e.g., axial, coronal, sagittal, etc.

The trained 2D segmentation network receives as input the one or more 2D slices and outputs a prediction map (or segmentation mask) representing results of the segmentation of the one or more lesions from the one or more 2D slices. The probability map is a pixel-wise heat map where the intensity value of each respective pixel corresponds to a probability or a score that the respective pixel depicts a lesion.

The trained 2D segmentation network may be implemented using any suitable machine learning based network, such as, e.g., an FCN (fully convolutional network) or a CNN (convolutional neural network). In one embodiment, the trained 2D segmentation network is based on a U-Net architecture. In accordance with the U-Net architecture, the trained 2D segmentation network comprises an encoder to model relevant imaging features and a decoder to generate the prediction map. The encoder may be implemented using 5 blocks comprising two 3×3 convolutions with batch normalization and ReLU (rectified linear unit). The decoder has the same number of convolution blocks as the encoder. The input to each decoding block is concatenated with the encoding features with the same resolution.

The trained 2D segmentation network is trained during a prior offline or training stage. In one embodiment, the trained 2D segmentation network is trained according to workflow 300 of FIG. 3, described in detail below.

At step 206, 2D features are extracted from results of the segmentation of the one or more lesions from the one or more 2D slices. In one example, the 2D features are extracted at block 108 of FIG. 1. In one embodiment, the 2D features comprise probability values extracted from the prediction map using a predefined kernel. In one example, the kernel is a 5×5 kernel. However, the kernel may be of any other suitable size. The 2D features may comprise any other suitable metric or statistic. For example, one could directly use a 25-dimensional probability value vector as a 2D feature in case of a 5×5 kernel. One could include arithmetic mean, variance or higher order statistics such as, e.g., skewness and kurtosis as 2D features.

At step 208, the one or more lesions are segmented from a 3D patch extracted from the 3D input medical image using a trained 3D segmentation network. In one example, the 3D patch is extracted at block 110 of FIG. 1 from 3D input medical image 102 and the lesions are segmented from the 3D patch at block 112 of FIG. 1. The 3D patch depicts the one or more lesions. The 3D patch may be extracted from the 3D input medical image via patch-wise sampling. In one embodiment, the 3D patch has a patch size of 96×96×96, but may be of any other suitable dimension. In one embodiment, the 3D patch is the full 3D input medical image.

The trained 3D segmentation network receives as input the 3D patch and outputs a prediction map (or segmentation mask) representing results of the segmentation of the one or more lesions from the 3D patch. The probability map is a voxel-wise heat map where the intensity value of each respective voxel corresponds to a probability or a score that the respective voxel depicts a lesion.

The trained 3D segmentation network may be implemented using any suitable machine learning based network, such as, e.g., an FCN or a CNN. In one embodiment, the trained 3D segmentation network is based on a U-Net architecture. The trained 3D segmentation network based on the U-Net architecture may be similar to the trained 2D segmentation network described above in connection with step 204 of FIG. 2. The trained 3D segmentation network is trained during a prior offline or training stage. In one embodiment, the trained 3D segmentation network is trained according to workflow 300 of FIG. 3, described in detail below.

At step 210, 3D features are extracted from results of the segmentation of the one or more lesions from the 3D patch. In one example, the 3D features are extracted at block 114 of FIG. 1. In one embodiment, the 3D features comprise probability values extracted from the prediction map using a predefined kernel. In one example, the kernel is a 5×5×5 kernel. However, the kernel may be of any other suitable size. The 3D features may comprise any other suitable metric or statistic.

At step 212, the extracted 2D features and the extracted 3D features are fused to generated final segmentation results. In one example, the extracted 2D features and the extracted 3D features are fused at block 116 of FIG. 1. In one embodiment, a trained fusion model is applied to generate a final prediction map as the final segmentation results. The trained fusion model characterizes the prediction biases of the trained 2D segmentation network and the trained 3D segmentation network.

The trained fusion model receives the extracted 2D features and the extracted 3D features as input and outputs the final prediction map. The final prediction map is a voxelwise heat map where the intensity value of each respective voxel corresponds to a probability or a score that the respective voxel depicts a lesion. The final prediction map may be generated by, e.g., concatenating the extracted 2D features and the extracted 3D features, adding the extracted 2D features and the extracted 3D features, averaging (or a weighted average) the extracted 2D features and the extracted 3D features, or any other suitable approach for combining the extracted 2D features and the extracted 3D features. In one embodiment, the final prediction map is generated based on the extracted 2D features and the extracted 3D features by a weighted vote (when using ensemble learning). The trained fusion model may be implemented using any suitable deep neural network or machine learning based method such as random forests or gradient boosted trees. One could utilize random forests or gradient boosted trees as a fusion model to recursively split the lesion voxel candidates (extracted from the probability maps of the 2D and 3D segmentation networks) into lesional voxels and false positive voxels. The trained fusion model is trained during a prior offline or training stage. In one embodiment, the trained fusion model is trained according to workflow 300 of FIG. 3, described in detail below.

At step 214, the final segmentation results are output. In one example, the final segmentation results are final prediction map 118 in FIG. 1. The final segmentation results can be output by, for example, displaying the final segmentation results on a display device of a computer system, storing the final segmentation results on a memory or storage of a computer system, or by transmitting the final segmentation results to a remote computer system. In one embodiment, additional medical imaging analysis tasks may be performed based on the final segmentation results.

Advantageously, embodiments described herein provide for a 2D pathway and a 3D pathway for automatic segmentation of lesions to simultaneously exploit high-resolution 2D context from full 2D slice images and through-plane features from 3D patches. To effectively characterize the biases and false positives/negatives of predictions from the 2D and 3D pathways, embodiments described herein provide for a fusion model that generates the final prediction map that characterizes the biases of each prediction map and maintains overall higher detection performance. By providing a more clinically relevant lesion and abnormality detection map by deep learning networks in brain image analysis, embodiments described herein have the potential to improve clinical workflows and enable better characterization of disease progressions. Embodiments described herein may be implemented in a semi-automated or fully-automated workflow to assist radiologists in identifying and segmenting brain lesions and other abnormalities on large-scale brain MRI images.

Figure 3:
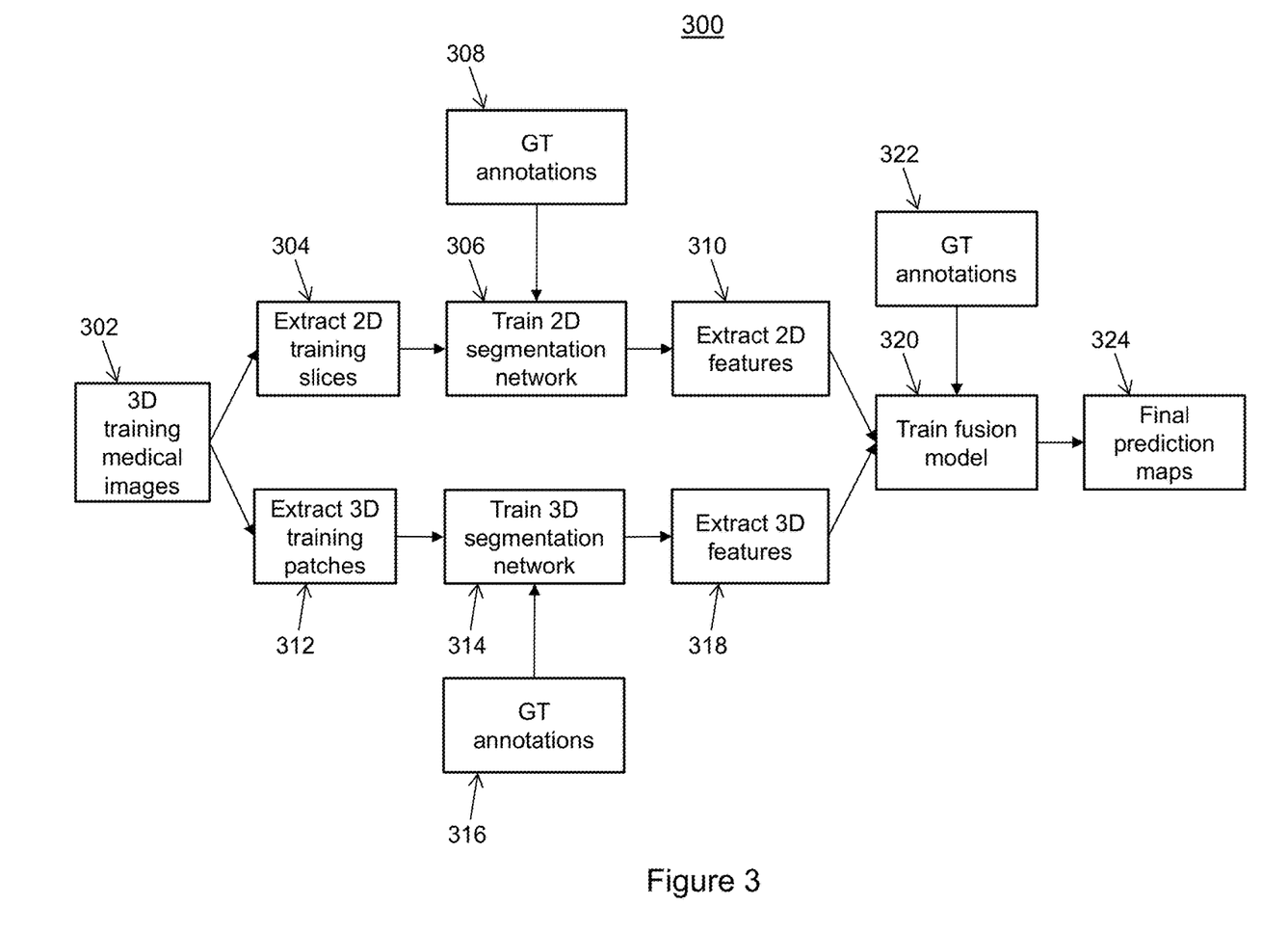
FIG. 3 shows a workflow for training machine learning based networks for automatic segmentation of lesions from a 3D medical image, in accordance with one or more embodiments.

FIG. 3 shows a workflow 300 for training machine learning based networks for automatic segmentation of lesions from a 3D medical image, in accordance with one or more embodiments. Workflow 300 may be performed during a prior offline or training stage to train a 2D segmentation network, a 3D segmentation network, and a fusion model. Once trained, the trained 2D segmentation network, trained 3D segmentation network, and trained fusion model may be applied during an online or testing stage. For example, the trained 2D segmentation network may be applied at step 204 of FIG. 2, the trained 3D segmentation network may be applied at step 208 of FIG. 2, and the trained fusion model may be applied at step 210 of FIG. 2.

At block 304, one or more 2D training slices are extracted from 3D training medical images 302. At block 306, the 2D segmentation network is trained to generate prediction maps based on the extracted 2D training slices and GT (ground truth) annotations 308 of the extracted 2D training slices. At block 310, 2D features (e.g., probability values) are extracted from the prediction maps. At block 312, 3D training patches are extracted from the 3D training medical images 302. At block 314, the 3D segmentation network is trained to generate prediction maps based on the extracted 3D training patches and GT annotations 316 of the extracted 3D patches. At block 318, 3D features (e.g., probability values) are extracted from the prediction map. At block 320, the fusion model is trained to generate final prediction maps 324 based on the 2D features and 3D features, as well as GT annotations 322 of the 2D features and the 3D features. The fusion model may be trained by any suitable approach. In one embodiment, the fusion model is trained by ensemble learning with random forests or boosted decision trees to effectively fuse the 2D features and the 3D features in a weakly supervised manner. The output prediction maps 324 are generated by a weighted vote (when using ensemble learning).

Figure 4:
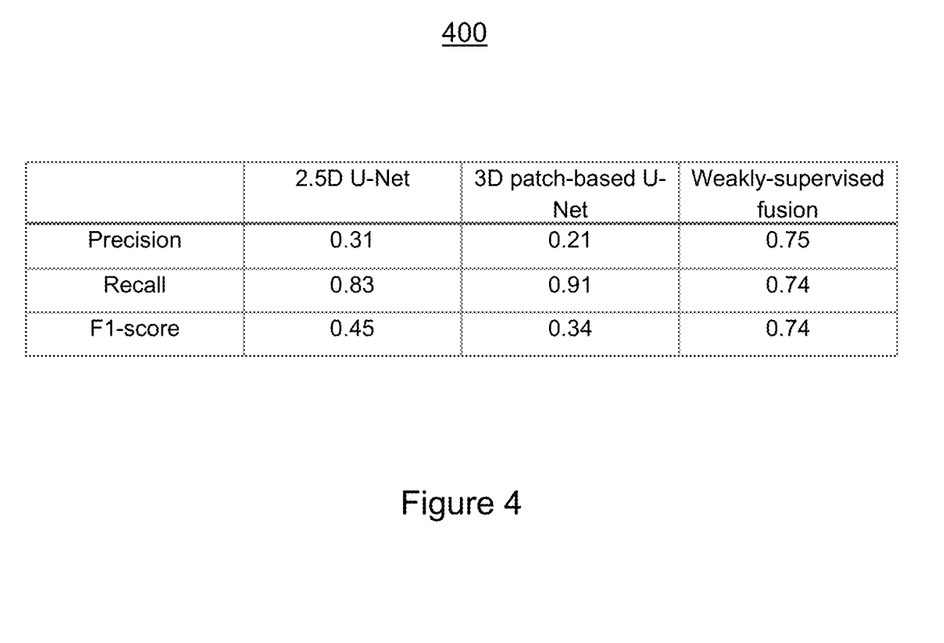
FIG. 4 shows a table comparing performance of a 2.5D U-Net and a 3D patch-based U-Net, with weakly supervised fusion of features extracted from results of the 2.5D U-Net and a 3D patch-based U-Net in accordance with embodiments described herein.

Embodiments described herein were experimentally validated. FIG. 4 shows a table 400 comparing performance of a 2.5D U-Net and a 3D patch-based U-Net, with weakly supervised fusion of features extracted from results of the 2.5D U-Net and a 3D patch-based U-Net in accordance with embodiments described herein. The results in table 400 were performed on MPRAGE images from 45 patients with brain metastases. As shown in table 400, the weakly-supervised fusion in accordance with embodiments described herein resulted in a significantly greater precision rate and balanced prediction between precision and recall, which led to a significantly higher F1-score over the 2.5D and 3D deep learning methods (29% compared to the 2.5D U-Net and 40% compared to the 3D patched-based U-Net).

Figure 5:
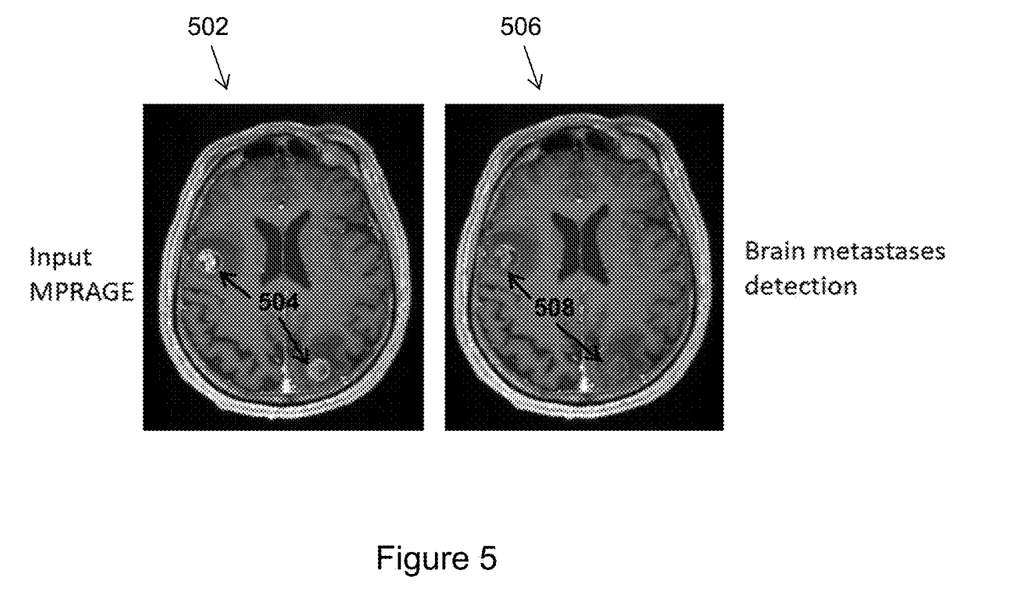
FIG. 5 shows an example of brain metastases detected in accordance with one or more embodiments.

FIG. 5 shows an example of brain metastases detected in accordance with one or more embodiments. Image 502 is an input MPRAGE image of a brain of a patient having brain metastases 504. Image 506 shows detected brain metastases 508 detected from image 502 in accordance with embodiments described herein.

Figure 6:
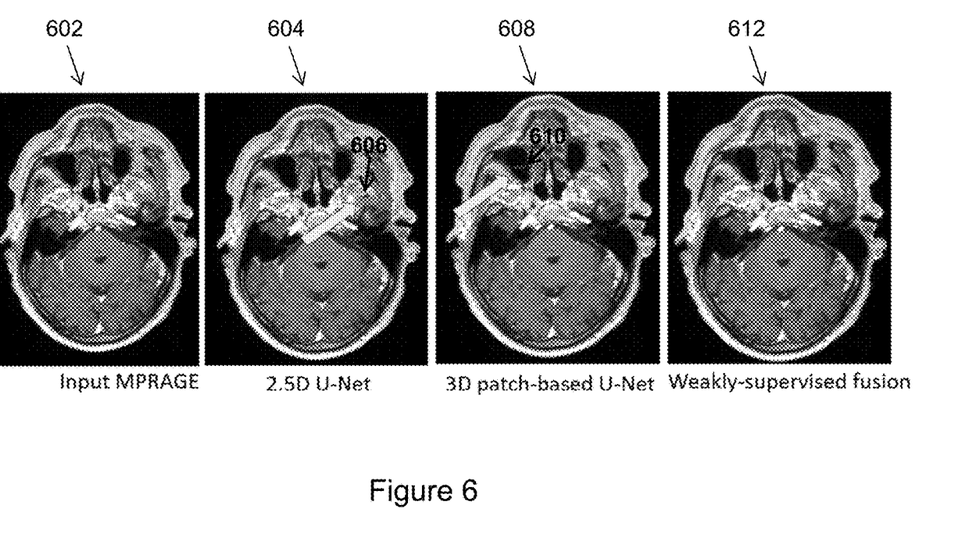
FIG. 6 shows an example of false positive reduction using embodiments described herein.

FIG. 6 shows an example of false positive reduction using embodiments described herein. Image 602 is an input MPRAGE image of a brain of a patient, which does not have brain metastases. Image 604 shows a false positive detected brain metastasis 606 detected from image 602 using a 2.5D U-Net. Image 608 shows a false positive detected brain metastasis 610 detected from image 602 using a 3D patch-based U-Net. Image 612 shows the detection of brain metastases in accordance with embodiments described herein. Image 612 does not include the false positive detected brain metastases 606 and 610.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, embodiments described herein are described with respect to methods and systems for automatic segmentation of lesions from medical images, as well as with respect to methods and systems for training machine learning based models (or networks) for automatic segmentation of lesions from medical images. Features, advantages or alternative embodiments herein can be assigned to the other claimed objects and vice versa. In other words, claims for methods and systems for training a machine learning based model can be improved with features described or claimed in context of the methods and systems for utilizing a trained machine learning based generator network, and vice versa.

In particular, the trained machine learning based models utilized in the methods and systems for automatic segmentation of lesions from medical images can be adapted by the methods and systems for training the machine learning based models.

Furthermore, the input data of the trained machine learning based models can comprise advantageous features and embodiments of the training input data, and vice versa. Furthermore, the output data of the trained machine learning based models can comprise advantageous features and embodiments of the output training data, and vice versa.

In general, a trained machine learning based model mimics cognitive functions that humans associate with other human minds. In particular, by training based on training data, the trained machine learning based model is able to adapt to new circumstances and to detect and extrapolate patterns.

In general, parameters of the machine learning based models can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based models can be adapted iteratively by several steps of training.

In particular, a trained machine learning based model can comprise a neural network, a support vector machine, a decision tree, and/or a Bayesian network, and/or the trained machine learning based model can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 7:
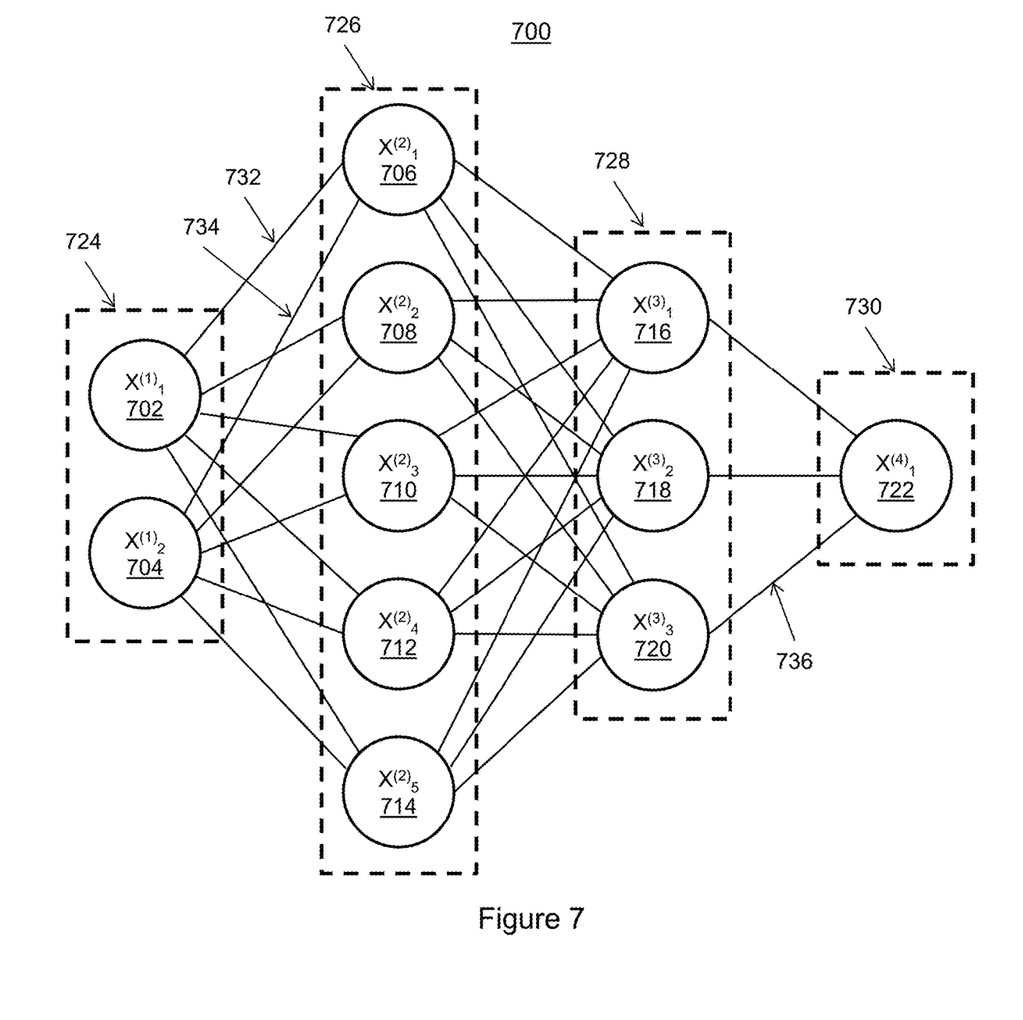
FIG. 7 shows an exemplary artificial neural network that may be used to implement one or more embodiments.

FIG. 7 shows an embodiment of an artificial neural network 700, in accordance with one or more embodiments. Alternative terms for "artificial neural network" are "neural network", "artificial neural net" or "neural net". Machine learning networks described herein, such as, e.g., the 2D segmentation network utilized at step 204 of FIG. 2, the 3D segmentation utilized at step 208 of FIG. 2, and the fusion model utilized at step 212 of FIG. 2, may be implemented using artificial neural network 700.

The artificial neural network 700 comprises nodes 702-722 and edges 732, 734, ..., 736, wherein each edge 732, 734, ..., 736 is a directed connection from a first node 702-722 to a second node 702-722. In general, the first node 702-722 and the second node 702-722 are different nodes 702-722, it is also possible that the first node 702-722 and the second node 702-722 are identical. For example, in FIG. 7, the edge 732 is a directed connection from the node 702 to the node 706, and the edge 734 is a directed connection from the node 704 to the node 706. An edge 732, 734, ..., 736 from a first node 702-722 to a second node 702-722 is also denoted as "ingoing edge" for the second node 702-722 and as "outgoing edge" for the first node 702-722.

In this embodiment, the nodes 702-722 of the artificial neural network 700 can be arranged in layers 724-730, wherein the layers can comprise an intrinsic order introduced by the edges 732, 734, ..., 736 between the nodes 702-722. In particular, edges 732, 734, ..., 736 can exist only between neighboring layers of nodes. In the embodiment shown in FIG. 7, there is an input layer 724 comprising only nodes 702 and 704 without an incoming edge, an output layer 730 comprising only node 722 without outgoing edges, and hidden layers 726, 728 in-between the input layer 724 and the output layer 730. In general, the number of hidden layers 726, 728 can be chosen arbitrarily. The number of nodes 702 and 704 within the input layer 724 usually relates to the number of input values of the neural network 700, and the number of nodes 722 within the output layer 730 usually relates to the number of output values of the neural network 700.

In particular, a (real) number can be assigned as a value to every node 702-722 of the neural network 700. Here, $x^{(n)}_i$ denotes the value of the i-th node 702-722 of the n-th layer 724-730. The values of the nodes 702-722 of the input layer 724 are equivalent to the input values of the neural network 700, the value of the node 722 of the output layer 730 is equivalent to the output value of the neural network 700. Furthermore, each edge 732, 734, ..., 736 can comprise a weight being a real number, in particular, the weight is a real number within the interval [−1, 1] or within the interval [0, 1]. Here, $w^{(m,n)}_{i,j}$ denotes the weight of the edge between the i-th node 702-722 of the m-th layer 724-730 and the j-th node 702-722 of the n-th layer 724-730. Furthermore, the abbreviation $w^{(n)}_{i,j}$ is defined for the weight $w^{(n, n+1)}_{i,j}$.

In particular, to calculate the output values of the neural network 700, the input values are propagated through the neural network. In particular, the values of the nodes 702-722 of the (n+1)-th layer 724-730 can be calculated based on the values of the nodes 702-722 of the n-th layer 724-730 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 724 are given by the input of the neural network 700, wherein values of the first hidden layer 726 can be calculated based on the values of the input layer 724 of the neural network, wherein values of the second hidden layer 728 can be calculated based in the values of the first hidden layer 726, etc.

In order to set the values $w^{(m,n)}_{i,j}$ for the edges, the neural network 700 has to be trained using training data. In particular, training data comprises training input data and training output data (denoted as $t_i$). For a training step, the neural network 700 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 700 (backpropagation algorithm). In particular, the weights are changed according to $$w_{i,j}'^{(n)} = w_{i,j}^{(n)} - \gamma \cdot \delta_j^{(n)} \cdot x_i^{(n)}$$

wherein $\gamma$ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 730, wherein f' is the first derivative of the activation function, and $y^{(n+1)}_j$ is the comparison training value for the j-th node of the output layer 730.

Figure 8:
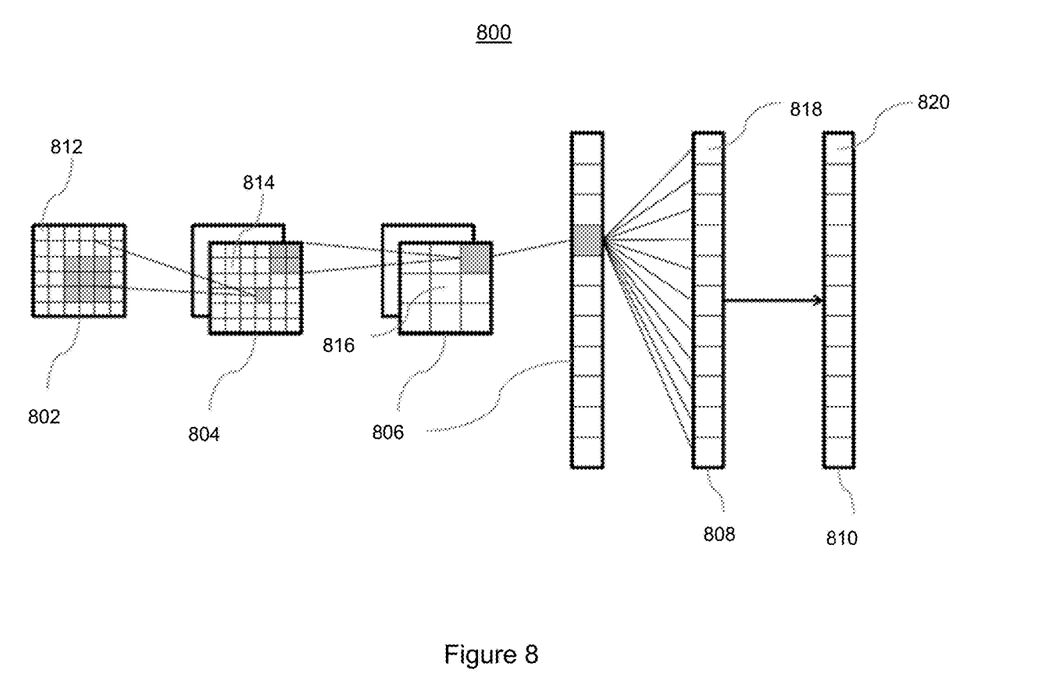
FIG. 8 shows a convolutional neural network that may be used to implement one or more embodiments.

FIG. 8 shows a convolutional neural network 800, in accordance with one or more embodiments. Machine learning networks described herein, such as, e.g., the 2D segmentation network utilized at step 204 of FIG. 2, the 3D segmentation utilized at step 208 of FIG. 2, and the fusion model utilized at step 212 of FIG. 2, may be implemented using convolutional neural network 800.

In the embodiment shown in FIG. 8, the convolutional neural network comprises 800 an input layer 802, a convolutional layer 804, a pooling layer 806, a fully connected layer 808, and an output layer 810. Alternatively, the convolutional neural network 800 can comprise several convolutional layers 804, several pooling layers 806, and several fully connected layers 808, as well as other types of layers. The order of the layers can be chosen arbitrarily, usually fully connected layers 808 are used as the last layers before the output layer 810.

In particular, within a convolutional neural network 800, the nodes 812-820 of one layer 802-810 can be considered to be arranged as a d-dimensional matrix or as a d-dimensional image. In particular, in the two-dimensional case the value of the node 812-820 indexed with i and j in the n-th layer 802-810 can be denoted as $x^{(n)}_{[i,j]}$. However, the arrangement of the nodes 812-820 of one layer 802-810 does not have an effect on the calculations executed within the convolutional neural network 800 as such, since these are given solely by the structure and the weights of the edges.

In particular, a convolutional layer 804 is characterized by the structure and the weights of the incoming edges forming a convolution operation based on a certain number of kernels. In particular, the structure and the weights of the incoming edges are chosen such that the values $x^{(n)}_k$ of the nodes 814 of the convolutional layer 804 are calculated as a convolution $x^{(n)}_k = K_k * x^{(n-1)}$ based on the values $x^{(n-1)}$ of the nodes 812 of the preceding layer 802, where the convolution * is defined in the two-dimensional case as $$x_k^{(n)}[i,j] = (K_k * x^{(n-1)})[i,j] = \Sigma_{i'} \Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 812-818 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 812-820 in the respective layer 802-810. In particular, for a convolutional layer 804, the number of nodes 814 in the convolutional layer is equivalent to the number of nodes 812 in the preceding layer 802 multiplied with the number of kernels.

If the nodes 812 of the preceding layer 802 are arranged as a d-dimensional matrix, using a plurality of kernels can be interpreted as adding a further dimension (denoted as "depth" dimension), so that the nodes 814 of the convolutional layer 804 are arranged as a (d+1)-dimensional matrix. If the nodes 812 of the preceding layer 802 are already arranged as a (d+1)-dimensional matrix comprising a depth dimension, using a plurality of kernels can be interpreted as expanding along the depth dimension, so that the nodes 814 of the convolutional layer 804 are arranged also as a (d+1)-dimensional matrix, wherein the size of the (d+1)-dimensional matrix with respect to the depth dimension is by a factor of the number of kernels larger than in the preceding layer 802.

The advantage of using convolutional layers 804 is that spatially local correlation of the input data can exploited by enforcing a local connectivity pattern between nodes of adjacent layers, in particular by each node being connected to only a small region of the nodes of the preceding layer.

In embodiment shown in FIG. 8, the input layer 802 comprises 36 nodes 812, arranged as a two-dimensional 6×6 matrix. The convolutional layer 804 comprises 72 nodes 814, arranged as two two-dimensional 6×6 matrices, each of the two matrices being the result of a convolution of the values of the input layer with a kernel. Equivalently, the nodes 814 of the convolutional layer 804 can be interpreted as arranges as a three-dimensional 6×6×2 matrix, wherein the last dimension is the depth dimension.

A pooling layer 806 can be characterized by the structure and the weights of the incoming edges and the activation function of its nodes 816 forming a pooling operation based on a non-linear pooling function f. For example, in the two dimensional case the values $x^{(n)}$ of the nodes 816 of the pooling layer 806 can be calculated based on the values $x^{(n-1)}$ of the nodes 814 of the preceding layer 804 as $$x^{(n)}[i,j] = f(x^{(n-1)}[id_1, jd_2], \ldots, x^{(n-1)}[id_1+d_1-1, jd_2+d_2-1])$$

In other words, by using a pooling layer 806, the number of nodes 814, 816 can be reduced, by replacing a number $d_1 \cdot d_2$ of neighboring nodes 814 in the preceding layer 804 with a single node 816 being calculated as a function of the values of said number of neighboring nodes in the pooling layer. In particular, the pooling function f can be the max-function, the average or the L2-Norm. In particular, for a pooling layer 806 the weights of the incoming edges are fixed and are not modified by training.

The advantage of using a pooling layer 806 is that the number of nodes 814, 816 and the number of parameters is reduced. This leads to the amount of computation in the network being reduced and to a control of overfitting.

In the embodiment shown in FIG. 8, the pooling layer 806 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 808 can be characterized by the fact that a majority, in particular, all edges between nodes 816 of the previous layer 806 and the nodes 818 of the fully-connected layer 808 are present, and wherein the weight of each of the edges can be adjusted individually.

In this embodiment, the nodes 816 of the preceding layer 806 of the fully-connected layer 808 are displayed both as two-dimensional matrices, and additionally as non-related nodes (indicated as a line of nodes, wherein the number of nodes was reduced for a better presentability). In this embodiment, the number of nodes 818 in the fully connected layer 808 is equal to the number of nodes 816 in the preceding layer 806. Alternatively, the number of nodes 816, 818 can differ.

Furthermore, in this embodiment, the values of the nodes 820 of the output layer 810 are determined by applying the Softmax function onto the values of the nodes 818 of the preceding layer 808. By applying the Softmax function, the sum the values of all nodes 820 of the output layer 810 is 1, and all values of all nodes 820 of the output layer are real numbers between 0 and 1.

A convolutional neural network 800 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 800 can be trained based on the backpropagation algorithm. For preventing overfitting, methods of regularization can be used, e.g. dropout of nodes 812-820, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-3. Certain steps or functions of the methods and workflows described herein, including one or more of the steps or functions of FIGS. 1-3, may be performed by a server or by another processor in a network-based cloud-computing system. Certain steps or functions of the methods and workflows described herein, including one or more of the steps of FIGS. 1-3, may be performed by a client computer in a network-based cloud computing system. The steps or functions of the methods and workflows described herein, including one or more of the steps of FIGS. 1-3, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-3, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 9:
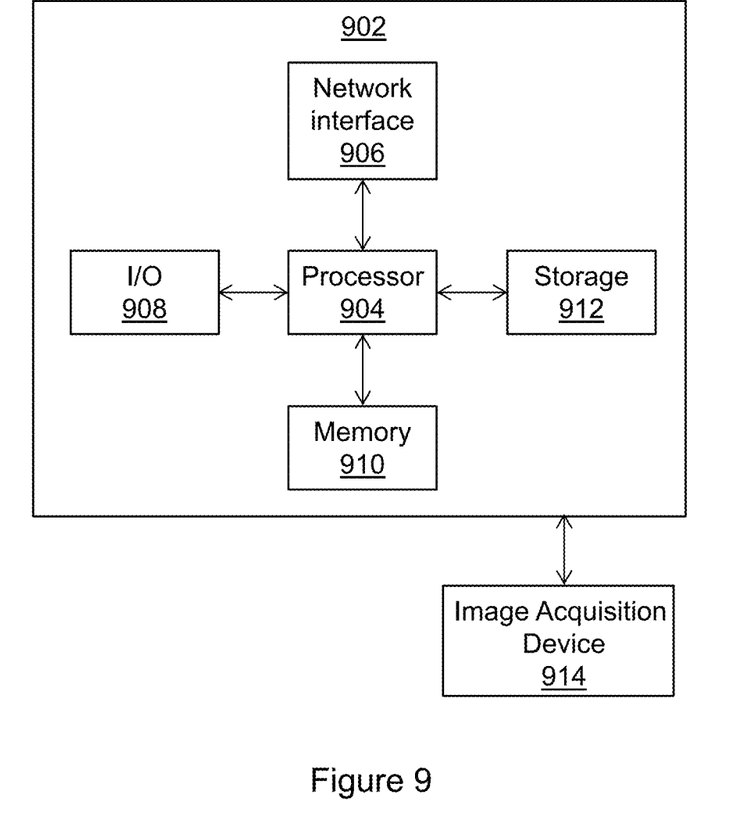
FIG. 9 shows a high-level block diagram of a computer that may be used to implement one or more embodiments.

A high-level block diagram of an example computer 902 that may be used to implement systems, apparatus, and methods described herein is depicted in FIG. 9. Computer 902 includes a processor 904 operatively coupled to a data storage device 912 and a memory 910. Processor 904 controls the overall operation of computer 902 by executing computer program instructions that define such operations. The computer program instructions may be stored in data storage device 912, or other computer readable medium, and loaded into memory 910 when execution of the computer program instructions is desired. Thus, the method and workflow steps or functions of FIG. 2 can be defined by the computer program instructions stored in memory 910 and/or data storage device 912 and controlled by processor 904 executing the computer program instructions. For example, the computer program instructions can be implemented as computer executable code programmed by one skilled in the art to perform the method and workflow steps or functions of FIGS. 1-3. Accordingly, by executing the computer program instructions, the processor 904 executes the method and workflow steps or functions of FIGS. 1-3. Computer 902 may also include one or more network interfaces 906 for communicating with other devices via a network. Computer 902 may also include one or more input/output devices 908 that enable user interaction with computer 902 (e.g., display, keyboard, mouse, speakers, buttons, etc.).

Processor 904 may include both general and special purpose microprocessors, and may be the sole processor or one of multiple processors of computer 902. Processor 904 may include one or more central processing units (CPUs), for example. Processor 904, data storage device 912, and/or memory 910 may include, be supplemented by, or incorporated in, one or more application-specific integrated circuits (ASICs) and/or one or more field programmable gate arrays (FPGAs).

Data storage device 912 and memory 910 each include a tangible non-transitory computer readable storage medium. Data storage device 912, and memory 910, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 908 may include peripherals, such as a printer, scanner, display screen, etc. For example, input/output devices 908 may include a display device such as a cathode ray tube (CRT) or liquid crystal display (LCD) monitor for displaying information to the user, a keyboard, and a pointing device such as a mouse or a trackball by which the user can provide input to computer 902.

Any or all of the systems and apparatus discussed herein, such as, e.g., the 2D segmentation network utilized at step 204 of FIG. 2, the 3D segmentation network utilized at step 208 of FIG. 2, and the fusion model utilized at step 212 of FIG. 2, may be implemented using one or more computers such as computer 902.

One skilled in the art will recognize that an implementation of an actual computer or computer system may have other structures and may contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
receiving a 3D input medical image depicting one or more lesions;
segmenting the one or more lesions from one or more 2D slices extracted from the 3D input medical image using a trained 2D segmentation network;
extracting first probability values from results of the segmentation of the one or more lesions from the one or more 2D slices;
segmenting the one or more lesions from a 3D patch extracted from the 3D input medical image using a trained 3D segmentation network;
extracting second probability values from results of the segmentation of the one or more lesions from the 3D patch;
fusing the first probability values and the second probability values using a trained machine learning based fusion model to generate final segmentation results, wherein the trained machine learning based fusion model is trained based on 1) probability values extracted from results of a segmentation of 2D training slices, 2) probability values extracted from results of a segmentation of 3D training images, and 3) ground truth annotations of the probability values extracted from the results of the segmentation of 2D training slices and the 3D training images; and
outputting the final segmentation results.

2. The method of claim 1, wherein:
extracting first probability values from results of the segmentation of the one or more lesions from the one or more 2D slices comprises extracting the first probability values from a prediction map output from the trained 2D segmentation network, and
extracting second probability values from results of the segmentation of the one or more lesions from the 3D patch comprises extracting the second probability values from a prediction map output from the trained 3D segmentation network.

3. The method of claim 1, further comprising:
training the trained machine learning based fusion model by ensemble learning.

4. The method of claim 1, wherein fusing the first probability values and the second probability values using a trained machine learning based fusion model to generate final segmentation results comprises:
concatenating the first probability values and the second probability values.

5. The method of claim 1, wherein fusing the first probability values and the second probability values using a trained machine learning based fusion model to generate final segmentation results comprises:
combining the first probability values and the second probability values based on a weighted vote.

6. The method of claim 1, wherein fusing the first probability values and the second probability values using a trained machine learning based fusion model to generate final segmentation results comprises:
fusing the first probability values and the second probability values to generate a final prediction map representing a voxelwise score that a voxel depicts a lesion.

7. The method of claim 1, wherein the one or more 2D slices comprises a plurality of orientation images.

8. The method of claim 1, wherein the 3D input medical image comprises an MM (magnetic resonance imaging) image of a brain of a patient and the one or more lesions comprises one or more brain metastases.

9. An apparatus comprising:
means for receiving a 3D input medical image depicting one or more lesions;
means for segmenting the one or more lesions from one or more 2D slices extracted from the 3D input medical image using a trained 2D segmentation network;
means for extracting first probability values from results of the segmentation of the one or more lesions from the one or more 2D slices;
means for segmenting the one or more lesions from a 3D patch extracted from the 3D input medical image using a trained 3D segmentation network;
means for extracting second probability values from results of the segmentation of the one or more lesions from the 3D patch;
means for fusing the first probability values and the second probability values using a trained machine learning based fusion model to generate final segmentation results, wherein the trained machine learning based fusion model is trained based on 1) probability values extracted from results of a segmentation of 2D training slices, 2) probability values extracted from results of a segmentation of 3D training images, and 3) ground truth annotations of the probability values extracted from the results of the segmentation of 2D training slices and the 3D training images; and
means for outputting the final segmentation results.

10. The apparatus of claim 9, wherein:
the means for extracting first probability values from results of the segmentation of the one or more lesions from the one or more 2D slices comprises means for extracting the first probability values from a prediction map output from the trained 2D segmentation network, and
the means for extracting second probability values from results of the segmentation of the one or more lesions from the 3D patch comprises means for extracting the second probability values from a prediction map output from the trained 3D segmentation network.

11. The apparatus of claim 9, further comprising:
means for training the trained machine learning based fusion model by ensemble learning.

12. The apparatus of claim 9, wherein the means for fusing the first probability values and the second probability values using a trained machine learning based fusion model to generate final segmentation results comprises:
means for concatenating the first probability values and the second probability values.

13. A non-transitory computer readable medium storing computer program instructions, the computer program instructions when executed by a processor cause the processor to perform operations comprising:
receiving a 3D input medical image depicting one or more lesions;
segmenting the one or more lesions from one or more 2D slices extracted from the 3D input medical image using a trained 2D segmentation network;
extracting first probability values from results of the segmentation of the one or more lesions from the one or more 2D slices;
segmenting the one or more lesions from a 3D patch extracted from the 3D input medical image using a trained 3D segmentation network;
extracting second probability values from results of the segmentation of the one or more lesions from the 3D patch;
fusing the first probability values and the second probability values using a trained machine learning based fusion model to generate final segmentation results, wherein the trained machine learning based fusion model is trained based on 1) probability values extracted from results of a segmentation of 2D training slices, 2) probability values extracted from results of a segmentation of 3D training images, and 3) ground truth annotations of the probability values extracted from the results of the segmentation of 2D training slices and the 3D training images; and
outputting the final segmentation results.

14. The non-transitory computer readable medium of claim 13, wherein:
extracting first probability values from results of the segmentation of the one or more lesions from the one or more 2D slices comprises extracting the first probability values from a prediction map output from the trained 2D segmentation network, and
extracting second probability values from results of the segmentation of the one or more lesions from the 3D patch comprises extracting the second probability values from a prediction map output from the trained 3D segmentation network.

15. The non-transitory computer readable medium of claim 13, wherein fusing the first probability values and the second probability values using a trained machine learning based fusion model to generate final segmentation results comprises:
combining the first probability values and the second probability values based on a weighted vote.

16. The non-transitory computer readable medium of claim 13, wherein fusing the first probability values and the second probability values using a trained machine learning based fusion model to generate final segmentation results comprises:
fusing the first probability values and the second probability values to generate a final prediction map representing a voxelwise score that a voxel depicts a lesion.

17. The non-transitory computer readable medium of claim 13, wherein the one or more 2D slices comprises a plurality of orientation images.

18. The non-transitory computer readable medium of claim 13, wherein the 3D input medical image comprises an MM (magnetic resonance imaging) image of a brain of a patient and the one or more lesions comprises one or more brain metastases.

* * * * *